US010441695B2

(12) United States Patent
Steingräber

(10) Patent No.: US 10,441,695 B2
(45) Date of Patent: Oct. 15, 2019

(54) DRIVE DEVICE FOR A MEMBRANE FLUID PUMP AND OPERATING METHOD

(71) Applicant: Berlin Heart GmbH, Berlin (DE)

(72) Inventor: Robert Steingräber, Berlin (DE)

(73) Assignee: BERLIN HEART GMBH, Berlin (DE)

( * ) Notice: Subject to any disclaimer, the term of this patent is extended or adjusted under 35 U.S.C. 154(b) by 0 days.

(21) Appl. No.: 16/293,888

(22) Filed: Mar. 6, 2019

(65) Prior Publication Data

US 2019/0275223 A1      Sep. 12, 2019

(30) Foreign Application Priority Data

Mar. 8, 2018  (EP) ..................................... 18160699

(51) Int. Cl.
*A61M 1/10* (2006.01)
*F04B 43/00* (2006.01)

(52) U.S. Cl.
CPC ............ *A61M 1/106* (2013.01); *A61M 1/107* (2013.01); *A61M 1/1008* (2014.02); *A61M 1/1081* (2013.01); *F04B 43/0081* (2013.01); *A61M 2205/3337* (2013.01); *F04B 2205/03* (2013.01)

(58) Field of Classification Search
None
See application file for complete search history.

(56) References Cited

U.S. PATENT DOCUMENTS 9,555,173 B2    1/2017  Spainer
2016/0250399 A1  9/2016  Tiller et al.

FOREIGN PATENT DOCUMENTS

| EP | 2 388 028 A1 | 11/2011 |
| EP | 2 860 399 A1 | 4/2015 |
| WO | WO 2011/018244 A1 | 2/2011 |
| WO | WO 2013/160411 A1 | 10/2013 |

*Primary Examiner* — Brian T Gedeon
(74) *Attorney, Agent, or Firm* — Brinks Gilson & Lione

(57) ABSTRACT

A drive device is provided comprising a working pump, the working pump connected to a membrane fluid pump, and the working pump having a working piston able to oscillate axially between two reversal points for contracting and expanding a working chamber, and a control unit for controlling a movement of the working piston between the two reversal points. The controlled movement of the working piston comprises three temporally successive phases, in a first phase the working piston is accelerated to a speed that is greater than a speed at the end of the first phase, in a second phase the working piston is moved such that a specified speed of the working piston, a specified relative pressure in the working chamber, or a specified force of the working piston is substantially kept constant, and in a third phase the working piston is moved at a negative acceleration.

24 Claims, 4 Drawing Sheets

DRIVE DEVICE FOR A MEMBRANE FLUID PUMP AND OPERATING METHOD

CROSS-REFERENCE TO RELATED APPLICATIONS

This application claims priority under 35 USC § 119 to European Patent Application No. 18 160 699.7, filed Mar. 8, 2018, which is hereby incorporated by reference.

DETAILED DESCRIPTION

Figure 1:
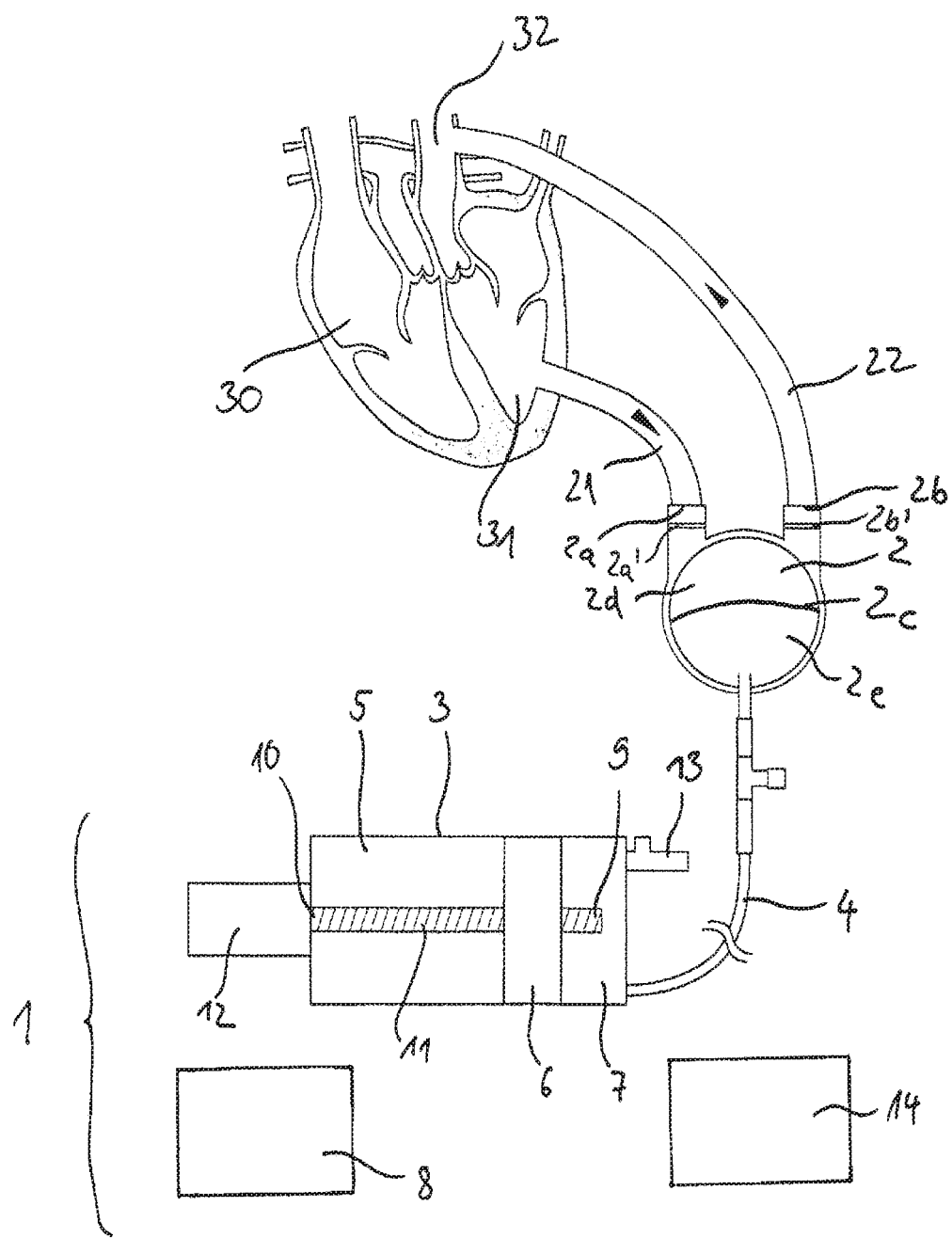
FIG. 1 is a schematic depiction of a cardiac support system according to the invention.

The present invention relates to a drive device for a membrane fluid pump, a pump system, and a cardiac support system, each containing such a drive device, and relates to a method for operating such a drive device.

Drive devices for membrane fluid pumps that are used as drive devices for membrane blood pumps in cardiac support systems are known from the prior art. These drive devices have a pneumatic cylinder that is connected to the membrane blood pump via a pressure line. A piston may be moved back and forth in the pneumatic cylinder in an oscillating manner between two reversal points. The movement of the piston causes the volume of a working chamber that is inside the pneumatic cylinder and that connects to the pressure line in a pressure exchange connection to increase and decrease. The working chamber furthermore has an equalizing valve via which the working chamber is connected to the environment for exchanging air. With this valve, air may be drawn into the working chamber when there is negative relative pressure and air may be discharged when there is positive relative pressure. The piston is moved by a spindle that is driven with an electric motor.

In particular, a drive device is known that is used for large blood pumps of 60 mL or greater displacement volume.

The objective of the present invention is therefore to provide a novel drive device for membrane fluid pumps, which drive device is in particular also suitable for small membrane fluid pumps.

Moreover, a corresponding method for operating the drive device, a corresponding pump system, and a corresponding cardiac support system containing the drive device are to be provided.

The drive device for a membrane fluid pump according to the invention comprises a working pump, the working pump being connected to the membrane fluid pump via a pressure line in order to drive the membrane fluid pump, and the working pump having a hollow cylinder and a working piston able to oscillate axially therein between two reversal points for contracting and expanding a working chamber in the working pump, the working chamber being in a pressure exchanging connection with the pressure line.

Moreover, the working pump according to the invention comprises a control unit for controlling a movement of the working piston between the reversal points. Controlling a movement of the working piston shall be construed here to mean a targeted influencing of the movement of the working piston so that a specified movement of the working piston or a specified state of the working pump is attained. In particular, controlling the movement of the working piston shall be construed to mean regulating for attaining the specified movement or the specified state.

The drive device according to the invention is characterized in that the controlled movement of the working piston comprises three temporally successive phases, in a first phase the working piston being accelerated to a speed that is greater than a speed at the end of the first phase, in a second phase the working piston being moved such that a specified speed of the working piston, a specified relative pressure in the working chamber, or a specified force of the working piston is largely kept constant, and in a third phase the working piston being moved at a negative acceleration.

In the following, accelerations shall be construed to mean a positive acceleration, that is, an increase in the speed in the direction of movement, if the mathematical operator for the acceleration is not explicitly stated. The pressure in the working chamber relative to the ambient pressure is called the relative pressure here. The force of the working piston may in particular include a load and an inertia of the working piston.

The first through third phases, also called compression phase, pumping phase, and braking phase, are run through within a half pump cycle, that is, once in the evacuation phase and once in the filling phase. The evacuation phase shall be construed here to be the phase in which the membrane fluid pump is evacuated by the movement of the working piston. The filling phase shall be construed here to be the phase in which the membrane fluid pump is filled due to the movement of the working piston. The first, second, and third phases may have different durations. In particular, the first phase may have a duration of ≥30% and/or ≤45%, preferably ≥35% and/or ≤40%, of the duration of one half of a pump cycle, the second phase may have a duration of ≥35% and/or ≤50%, preferably ≥40% and/or ≤45%, of the duration of one half of a pump cycle, and the third phase may have duration of ≥1% and/or ≤16%, preferably ≥5% and/or ≤10%, more preferably 8%, of the duration of one half of a pump cycle. The durations of the compression phase and of the pumping phase may also be variable and/or may be a function of state variables for the working pump. For example, the durations may be a function of the relative pressure in the working chamber or of a completed piston stroke. For example, in a case in which in the second phase, that is the pumping phase, the working piston is moved such that a predefined relative pressure is kept constant, the preceding compression phase may last until a predefined piston position is attained in the working chamber.

Moreover, the three phases may be separated from one another by a transition phase, the first and second phases being separated from one another by a first transition phase, the second and third phases being separated from one another by a second transition phase, and the third and first phases being separated from one another by a third transition phase. The transition phases maintain the steadiness of the acceleration of the working piston so that the working piston is able to move smoothly and with a low load. The transition phases may have the same or different durations. If the durations of the transition phases are the same, the duration of a transition phase may be ≥2% and/or ≤10%, in particular ≥3% and/or ≤6%, particularly preferably 4% of the duration of half a pump cycle.

Furthermore, it is conceivable for two or all of the first through third phases to immediately follow one another. The total of the durations of all occurring phases is then equal to the duration of the evacuation and filling phases. The duration of the evacuation and filling phases are then also called the evacuation period and the filling period.

The drive device according to the invention is in particular suitable for driving small membrane fluid pumps. Controlling the movement of the working piston of the drive device according to the three phases enables high pump performance and a low risk of blood damage by the membrane fluid pump. The high pump performance is in particular attained in that initially, in the first phase, a specific pump speed, a specific pump pressure, or a specific pump force is attained rapidly. At the beginning, only a small amount of energy has to be applied by the drive device, since the relative pressure in the working chamber is still low at the beginning of the first phase and supports the movement of the working piston. This increases the efficiency of the drive device. The second phase of constant pump speed, constant pump pressure, or constant pump force permits efficient transfer of the pump energy to the membrane fluid pump, uniform pumping of the membrane fluid pump, and thus a uniform flow of the fluid out of and into the membrane fluid pump. Due to the uniform flow of the fluid, the risk of blood damage in particular is also reduced. In the third phase, the working piston is decelerated in order to then be moved in the opposite direction following reversal.

The control unit may in particular be configured to control the movement of the working piston such that in the first phase the working piston is accelerated to a speed that is at least 1.2 times greater than the speed at the end of the first phase, preferably at least 1.6 times greater and at most 15 times greater, preferably at most 7 times greater. Moreover, the control unit may be configured to control the movement of the working piston such that in the first phase the working piston is moved at linearly decreasing acceleration. This permits position or speed-regulated operation in which differences due to production or wear may be compensated. In addition, a peak speed may be limited to a target value and the position specification may be adapted to the connected pump-cannula combination with only one parameter.

The control unit may furthermore be configured to control the movement of the working piston such that in the third phase the working piston is moved at a substantially constant negative acceleration. This makes it possible to brake the working piston slowly, so that a peak acceleration and a flow may be limited.

The third phase may in particular terminate with a stop of the working piston, after which the working piston is moved again in the opposite direction. Stop here means a speed of zero, but does not necessarily mean an acceleration equal to zero.

The drive device may preferably comprise an electric motor for driving the working piston. In particular the electric motor may comprise a spindle, in particular a ball screw spindle or a ball-type linear drive, that is configured to transmit a torque of the motor to the working piston such that the working piston executes a translatory movement between the reversal points. There is preferably a fixed kinematic relationship v=const. * n between a speed n of the spindle and the speed v of the working piston.

The control unit may be configured to control the movement of the working piston according to a temporal position specification for the working piston, the speed of the working piston being maintained substantially constant in the second phase. Control of the movement of the working piston according to the temporal position specification shall be construed in particular to mean a regulation (also with position regulation) in which the temporal position specification is a controlled variable. Controlling the movement according to a position specification is less susceptible to failure in terms of load changes and leakage. For example, an incorrect relative pressure in the working chamber does not lead directly to an incorrect movement of the working piston. Another advantage of controlling the movement of the working piston according to a position specification is that the working piston is controlled according to the position specification regardless of pressure, even with increasing load. When controlling according to a pressure specification, the air volume displaced in this case would be reduced. When controlling according to position specification, with increasing load the blood flow therefore does not decrease as sharply as would be the case with controlling according to pressure specification. Furthermore, mechanical differences of different working pumps may be compensated, so that the blood flow becomes more reproducible and more uniform.

In addition or alternatively, the control device may be configured to control the movement of the working piston according to a temporal relative pressure specification for the working chamber, the relative pressure in the working chamber being kept substantially constant in the second phase. Control of the movement of the working piston according to the temporal relative pressure specification shall be construed in particular to mean a regulation (also with pressure regulation or relative pressure regulation) in which the temporal relative pressure specification is a controlled variable. Control according to a pressure specification is advantageous in that this type of control is already known from the prior art to users of drives with pressure tanks and parameters may be adjusted more intuitively. An additional advantage of pressure regulation is that in the filling phase it is possible to set a uniformly low filling pressure and thus reduce the risk of blood damage. Moreover, the duration of the pumping phase may be kept variable so that the beginning and/or the end of the pumping phase may be made a function of a position of the working piston.

In addition or alternatively to control according to the temporal position specification and/or relative pressure specification, the control unit may be configured to control the movement of the working piston according to a temporal force specification for the working piston, the force for the working piston being kept substantially constant in the second phase. Control of the movement of the working piston according to the temporal force specification shall be construed in particular to mean regulation (also with force regulation) in which the temporal force specification is a controlled variable. As with control according to the relative pressure specification, parameters may be adjusted more intuitively. As with control according to the position specification, the fluid flow with control according to a force specification is not immediately disrupted by changes in load, since the force to required for accelerating the working piston is used to increase the relative pressure at the beginning of a half pump cycle. Furthermore, mechanical differences in different working pumps may be compensated, so that the blood flow is more reproducible and more uniform.

The control unit may furthermore be configured to combine the control according to position specification, the control according to relative pressure specification and/or according to force specification. For example, the control unit may be configured to determine the temporal position specification based on the temporal relative pressure specification and to control the movement of the working piston according to the position specification. Using a position specification with such a basis it is possible to compensate mechanical differences, to build up a minimum pressure without pressure feedback, to take into consideration conditions for the position specification and the speed specification, and to specify a stroke volume (that is, the volume of the working chamber covered by the working piston in a half pump cycle) and a dead volume (that is, a volume of the working chamber between a reversal point at the end of the evacuation phase and the cylinder wall that is not covered by the working piston), and a target pressure (maximum pressure) for the pumping phase, a flow and speed reserve, a rapid pressure change, a minimum speed, and a smooth movement.

Moreover, the control unit may be configured to switch between controlling the movement of the working piston according to the temporal position specification, controlling the movement of the working piston according to the temporal relative pressure specification, and/or controlling the movement of the working piston according to the temporal force specification. In this case, the control unit may be configured to control the movement of the working piston according to the position specification in the first and third phases and according to the relative pressure specification and/or according to the force specification in the second phase. This permits the advantages of the different regulating concepts of position, relative pressure, and force regulation to be used in each of the three phases. In this way the working pump may run through, in a highly reproducible and stable manner, the specified position, relative pressure, and force specifications and may maintain a peak speed and/or a peak acceleration, which is difficult to attain with pressure or force regulation at low relative pressures. Due to the relative pressure regulation and force regulation in the second phase, the working pump in the second phase is focused directly on the user objective.

According to another variant, the control unit may be configured to determine the position specification based on a curve measurement of the relative pressure from preceding pump cycles. The advantage of this iteratively learning position regulation is that it is not necessary to switch between different regulators for the piston movement, but instead robust stable position regulation is used continuously. However, due to the use of the measured pressure curves, the position specification is adapted slowly such that the pressure objectives of the user are attained despite slow changes in load. Short-term disturbances are not followed, in contrast to pressure regulation.

Furthermore, the control unit may be configured to determine the temporal force specification based on the temporal position specification and to control the movement of the working piston according to the force specification. For example, a difference between a specified piston stroke and an attained piston stroke may be measured by means of a position sensor and the force of the working piston may be adjusted for the next pump cycle such that the difference is reduced in the next pump cycle.

Moreover, the control unit may be configured to control the movement of the working piston according to a temporal relative pressure specification for the working chamber and to control a temporal speed specification for the working piston. In this way a maximum speed may be established for the spindle in a simple manner and thus an assured specification for the maximum speed may be maintained.

The temporal position specification may also include a temporal speed specification and/or a temporal acceleration specification. The control unit may be configured to simultaneously control the movement of the working piston according to the temporal position specification, according to the temporal speed specification, and/or according to the temporal acceleration specification.

It is particularly advantageous when the working pump comprises an equalizing valve for changing an air mass and/or a relative pressure in the working chamber. The control unit may then be configured to control the equalizing valve according to a specification for the air mass, wherein the specification for the air mass may in particular comprise keeping the air mass constant. The control unit may also be configured to control the equalizing valve according to a specification for a mean relative pressure, wherein the specification comprises in particular keeping the mean relative pressure constant. Moreover, the control device may be configured to control the equalizing valve according to a specification for the relative pressure, a specification for a mean evacuation pressure, and/or a specification for a mean filling pressure. The control unit may also be configured to control the equalizing valve according to a relative pressure specification and/or a specification for one of the two or both reversal points. Controlling the equalizing valve shall be construed here to mean in particular opening and closing the equalizing valve at specific times. In addition, controlling the equalizing valve according to a relative pressure specification or air mass specification shall be construed to mean regulating in which, for example, an opening time for the equalizing valve is set as the control variable such that an air mass specification or relative pressure specification may be followed as control variable.

One advantageous embodiment of the drive device according to the invention provides that the control unit is configured to control the movement of the working piston according to the temporal position specification and simultaneously to control the equalizing valve according to the specification for the mean relative pressure.

Another advantageous embodiment of the drive device according to the invention provides that the control unit is configured to control the movement of the working piston, on the one hand, according to the temporal relative pressure specification or according to the temporal force specification, and, on the other hand, simultaneously to control the equalizing valve such that the dead volume is minimal, without the working piston striking the wall of the hollow cylinder. The dead volume may be kept low by specifying the reversal position near the wall at the end of the evacuation phase.

The control unit may furthermore be configured to determine the temporal position specification based on a reference trajectory of the working piston, wherein the reference trajectory takes into consideration a specified duration of the first phase, a specified duration of the second phase, a specified change in the acceleration of the piston in the first phase, a specified piston stroke, a specified maximum relative pressure, a specified pump rate, a specified relative evacuation duration, a specified filling degree, a specified evacuation degree, specified characteristic values for a membrane fluid pump to be connected, in particular a displacement volume of the membrane fluid pump, specified characteristic values for an inlet cannula that may be connected to the membrane fluid pump, and/or specified characteristic values for an outlet cannula that may be connected to the membrane fluid pump.

Using the reference trajectory, therefore, important conditions to be maintained by the entire system may be specified, and the position specification may be determined while satisfying the conditions. The dead volume of the cylinder may be specified to be minimal using the position specification in order to maintain maximum efficiency of the working pump. By specifying the piston stroke, the reversal point at the end of the filling phase, and thus also a stroke volume, may be set, that is the volume the working piston passes through in one half pump cycle. Thus the working piston moves within the set reversal points. In addition, it is particularly advantageous when the specified maximum pressure is as low as possible in order not to damage the fluid pumped through the membrane fluid pump that can be attached to the drive device. By specifying an evacuation degree and filling degree, as well as the pump rate, the desired fluid flow to be pumped from the membrane fluid pump may be set or may be adjusted to the fluid system to be connected to the membrane fluid pump. Furthermore, the transition phases between each of the three phases may be configured such that the working piston is able to move smoothly and with a low load. By providing the characteristic values for the membrane fluid pump and the cannulas, a trajectory may be adjusted to a specific pump-cannula combination.

The control unit may furthermore be configured, for controlling the movement of the working piston according to the temporal position specification, to determine a drive current strength for the spindle motor based on an estimated required torque for the spindle motor, wherein a load of the working piston, inertia of the working piston, estimated friction of the working piston, and/or a torque correction enter into the torque for compensating a position deviation and/or a speed deviation of the working piston from the temporal position specification. Greater position accuracy may be attained by taking the load, inertia, and friction of the working piston into consideration.

In particular, the control device may be configured to determine the inertia based on an acceleration resulting from the reference trajectory, to determine the load based on a measured relative pressure, and to estimate the friction based on a measured speed and/or a measured position.

The drive device may furthermore be embodied such that, during operation of the drive device, an instantaneous position and/or an instantaneous speed of the working piston may be measured by means of a position sensor. The control unit may then be configured to determine a position deviation and/or a speed deviation from the temporal position specification, to determine the torque correction based on the position deviation and/or the speed deviation, and to adjust the drive current strength such that the position deviation and/or the speed deviation of the working piston is reduced by the temporal position specification. In this way the drive device may compensate position deviations of the working piston, and the working piston may follow the desired course. By monitoring the estimated torque using the friction, occurrences of wear on the working piston may be detected during operation. The drive current strength may then be corrected appropriately.

The serviceability of the drive device according to the invention is increased when the drive device has a user interface by means of which user-specific parameters may be set during operation, in particular degree of filling and/or degree of evacuation of the membrane fluid pump, a piston stroke, a mean relative pressure, a relative evacuation duration, an evacuation pressure, a filling pressure, and/or a pump rate. The control unit may then be configured to adjust the temporal position specification, the temporal relative pressure specification, and/or the temporal force specification for controlling the movement of the working piston and/or to adjust the specification for the air mass, the specification for the relative pressure, and/or the specification for the air mass at one of the two or at both reversal points for controlling the equalizing valve during operation to a change in the user-specific parameters.

Moreover, the control unit may be configured to set a filling degree for the membrane fluid pump by changing a piston stroke and controlling the equalizing valve according to a specification for the mean evacuation pressure in the working chamber or by changing the mean relative pressure using the equalizing valve. An increase or reduction in the degree of filling may thus occur either due to an increase or a reduction in the piston stroke if there is still a stroke reserve, and keeping the mean evacuation pressure constant, or due to a drop or increase in the mean relative pressure if there is no more stroke reserve. The control unit may likewise be configured to set a degree of evacuation by changing a piston stroke and controlling the equalizing valve according to a specification for the mean filling pressure in the working chamber and/or by changing the mean relative pressure using the equalizing valve. An increase or decrease in the evacuation degree may thus occur either by increasing or a decreasing the piston stroke, if there is still a stroke reserve, and keeping the filling pressure constant, or by increasing or dropping the mean relative pressure, if there is no more stroke reserve.

The present invention also includes a pump system that comprises a membrane fluid pump, an inlet cannula, connected to the membrane fluid pump, for supplying a fluid to the membrane fluid pump, an outlet cannula, connected to the membrane fluid pump, for conducting a fluid out of the membrane fluid pump, and a drive device, described in the foregoing, for the membrane fluid pump.

The present invention furthermore includes a cardiac support system that comprises a membrane blood pump as a membrane fluid pump, an inlet cannula, connected to the membrane blood pump, for supplying blood from a ventricle and/or atrium of the heart to the membrane blood pump, an outlet cannula, connected to the membrane blood pump, for conducting the blood out of the membrane blood pump into a blood vessel, and a drive device, described in the foregoing, for the membrane blood pump.

Furthermore, according to the invention is a method for operating the drive device described in the foregoing for a membrane fluid pump, the movement of the working piston being controlled such that the movement comprises three temporally successive phases, in a first phase the working piston being accelerated to a speed that is greater than a speed at the end of the first phase, in the second phase the working piston being moved such that a predefined speed of the working piston, a predefined relative pressure in the working chamber, or a predefined force of the working piston is largely kept constant, and in a third phase the working piston being moved at a substantially constant negative acceleration.

The force may in particular include a load and an inertia of the working piston.

The method may furthermore comprise that the movement of the working piston is controlled such that in the first phase the working piston is moved at a linearly decreasing acceleration.

According to one advantageous embodiment of the method according to the invention, the movement of the working piston is controlled according to a temporal position specification for the working piston, the speed of the working piston being kept substantially constant in the second phase.

Alternatively or in addition to the aforesaid embodiment, according to another advantageous embodiment, the movement of the working piston is controlled according to a temporal relative pressure specification for the working chamber, the relative pressure in the working chamber being largely kept constant in the second phase.

Alternatively or in addition to the two aforesaid embodiments, according to another advantageous embodiment, the movement of the working piston is controlled according to a temporal force specification for the working piston, the force of the working piston being largely kept constant in the second phase.

The method may furthermore comprise that control according to the position specification, control according to the relative pressure specification, and/or control according to the force specification may be combined. For example, the method may comprise that the movement of the working piston is controlled in that the temporal position specification is determined based on the temporal relative pressure specification, and the movement of the working piston is controlled according to the temporal position specification.

As another variant, the method may comprise that the movement of the working piston in the first phase and in the third phase is controlled according to the temporal position specification and in the second phase is controlled according to the temporal relative pressure specification and/or the temporal force specification. As another variant, the method may comprise that the position specification is determined based on a curve measurement of the relative pressure from preceding pump cycles.

As another variant, the method may comprise that the temporal force specification is determined based on a temporal position specification, and the movement of the working piston is controlled according to the force specification. For example, a difference between a specified piston stroke and an attained piston stroke may be measured by means of a position sensor and the force of the working piston may be adjusted for the next pump cycle such that the difference is reduced in the next pump cycle.

The method may furthermore comprise that the movement of the working piston is controlled according to the temporal position specification and simultaneously that the equalizing valve is controlled according to a specification for the mean relative pressure. The variant of the method is not very susceptible to faults and has reproducible pump behavior, since, for one thing, the position regulation and the regulation of the mean relative pressure may be temporally decoupled, so that the variant is robust with respect to changes in load. The relative pressure may be increased as loads increase. An increase in stroke compensates sensitivity to decreasing load. In addition, the supplied or removed air mass may be better controlled using the measurement of the mean relative pressure, so that reproducible complete filling and evacuating that are not susceptible to faults are rendered possible. Due to the regulation of the mean relative pressure, it is thus even possible to rapidly detect and compensates interferences due to leakage and changes in load.

Alternatively, or additionally, the method may comprise that the movement of the working piston is controlled, on the one hand, according to the temporal relative pressure specification or according to the temporal force specification, and, on the other hand, the equalizing valve is simultaneously controlled such that the dead volume is minimal, without the working piston striking the wall of the hollow cylinder. Minimizing the air mass at the reversal point at the end of the evacuation phase has two advantages. First, during control according to the relative pressure specification or force specification it is necessary to specify the reversal points, because otherwise there is the risk that the working piston will run against the wall of the hollow cylinder. Secondly, the efficiency of the working pump is greater when the dead volume is minimal. Movement control according to the relative pressure specification has the advantage that a reserve for load changes may be set separately for filling and evacuating. Movement control according to the force specification has the advantage has the advantage that a reserve for load changes may be set separately for filling and evacuating and the relative pressure is increased as loads increase.

The method may furthermore comprise that the equalizing valve is controlled according to a specification for a mean evacuation pressure and/or a specification for a mean filling pressure independent of one another.

The method may furthermore comprise that the temporal position specification is determined based on a reference trajectory for the working piston. The reference trajectory may take into consideration a specified duration of the first phase, a specified duration of the second phase, a specified change in the acceleration of the working piston in the first phase, a specified piston stroke, a specified maximum relative pressure, a specified pump rate, a specified relative evacuation duration, a specified filling degree, a specified evacuation degree, specified characteristic values for a membrane fluid pump to be connected, in particular a displacement volume of the membrane fluid pump, specified characteristic values for an inlet cannula that may be connected to the membrane fluid pump, and/or specified characteristic values for an outlet cannula that may be connected to the membrane fluid pump.

The method may furthermore comprise that, for controlling the movement of the working piston according to the position specification, a drive current strength is determined for the spindle motor. The determination of the drive current strength may be based on an estimated required torque for the spindle motor. A load of the working piston, inertia of the working piston, estimated friction of the working piston, and/or a torque correction for compensating a position deviation and/or a speed deviation of the working piston from the temporal position specification may enter into the torque. The friction includes in particular static friction and slide friction. Taking the friction into consideration allows for faults due to mechanical wear to be detected and compensated more rapidly.

The method may in particular comprise determining the inertia based on an acceleration resulting from the reference trajectory, determining the load based on a measured relative pressure, and estimating the friction based on a measured speed and/or a measured position.

The method may furthermore comprise that during operation an instantaneous position and/or an instantaneous speed of the working piston is measured by means of a position sensor. The method may furthermore comprise that a position deviation and/or a speed deviation from the temporal position specification is determined, the torque correction is determined based on the position deviation and/or the speed deviation, and the drive current strength is adjusted such that the position deviation and/or the speed deviation of the working piston from the temporal position specification is reduced.

The method may furthermore comprise that during operation user-specific parameters may be set, in particular degree of filling and/or degree of evacuation of the membrane fluid pump, a piston stroke, a mean relative pressure, a relative evacuation duration, an evacuation pressure, a filling pressure, and/or a pump rate. The method may furthermore comprise that the temporal position specification, the temporal relative pressure specification, and/or the temporal force specification, for controlling the movement of the working piston and/or the specification for the air mass and/or the specification for the relative pressure for controlling the equalizing valve during operation may be adjusted to a change in the user-specific parameters.

The method may furthermore comprise that a specified filling degree of the membrane fluid pump may be set by changing a piston stroke and controlling the equalizing valve according to a specification for a mean evacuation pressure in the working chamber or by changing the relative pressure using the equalizing valve. The method may in particular comprise that the filling degree is increased or decreased in that the piston stroke is increased or decreased, if there is still a stroke reserve, and the mean evacuation pressure is kept constant, or in that the mean relative pressure is reduced or increased if there is no more stroke reserve.

The method may furthermore comprise that a specified evacuation degree is set by changing a piston stroke and controlling the equalizing valve according to a specification for a mean filling pressure in the working chamber or by changing the mean relative pressure using the equalizing valve. The method may in particular comprise that the evacuation degree is increased or decreased in that the piston stroke is increased or decreased, if there is still a stroke reserve, and the mean filling pressure is kept constant, or in that the mean relative pressure is increased or reduced if there is no more stroke reserve.

A drive device according to the invention, a cardiac support system according to the invention, and a method for operating the drive device are described in the following in detail using figures. Different elements essential to the invention or advantageously refining elements are identified in the context of a specific example, it also be possible to use individual elements from these elements as such for refining the invention, even removed from the context of the specific example and other features of the specific example. In addition, the same or similar reference numbers are used in the figures for identical or similar elements, and the explanation for them is therefore omitted in some cases.

Figure 2:
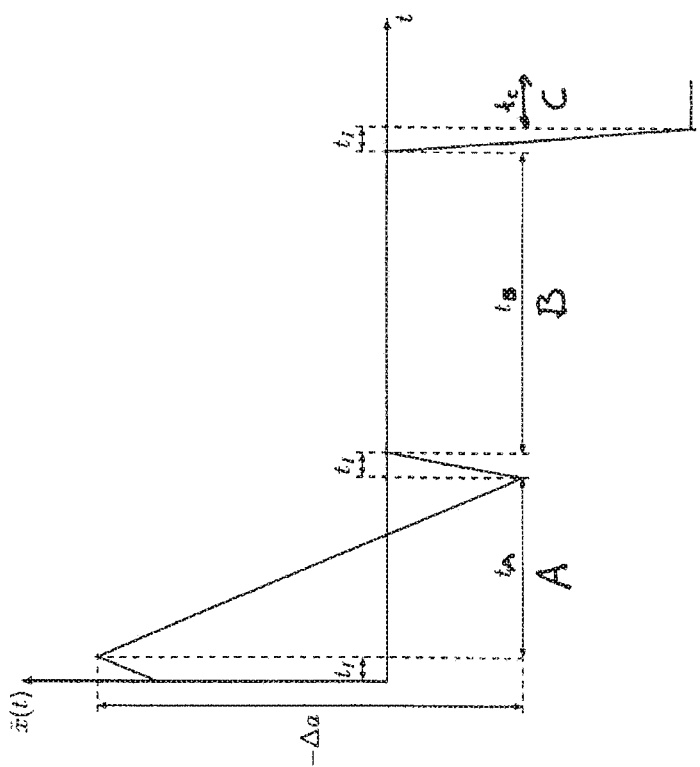
FIG. 2 is an acceleration-time diagram having a schematically depicted acceleration curve for the working piston of a drive device according to the invention during a half pump cycle.
Figure 3:
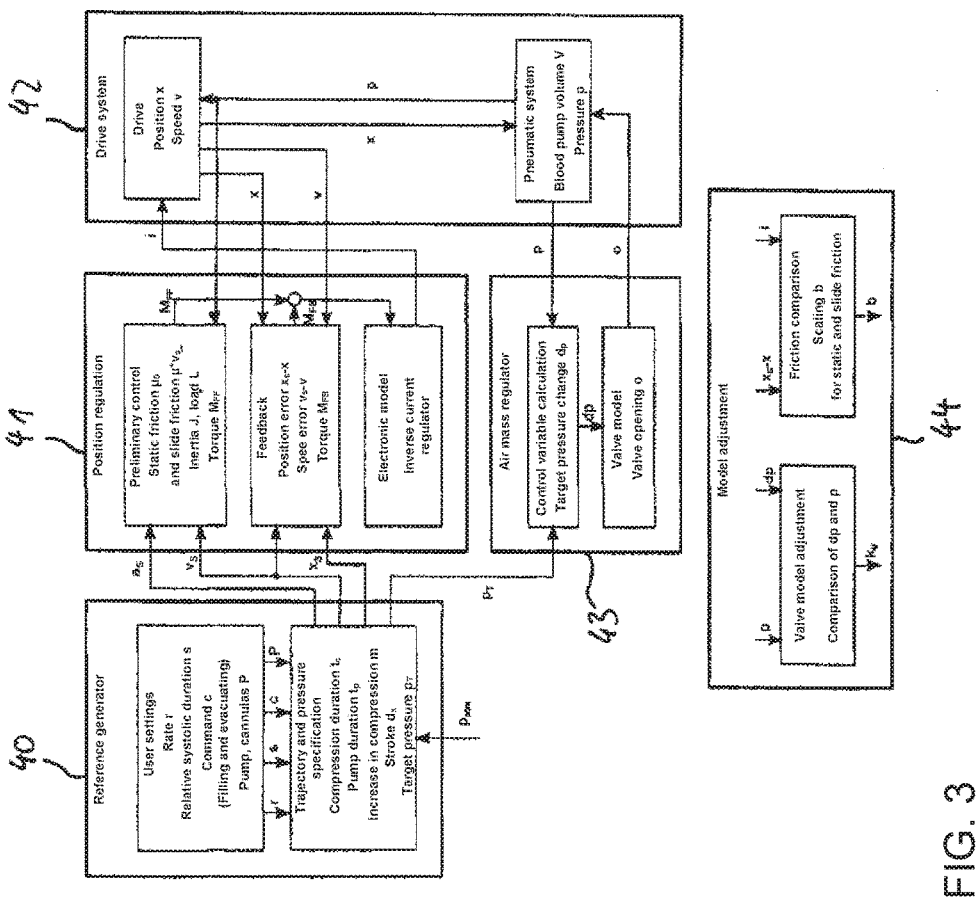
FIG. 3 is a flowchart for determining the position specification, the position regulation, and the regulation for the mean relative pressure according to the invention.
Figure 4:
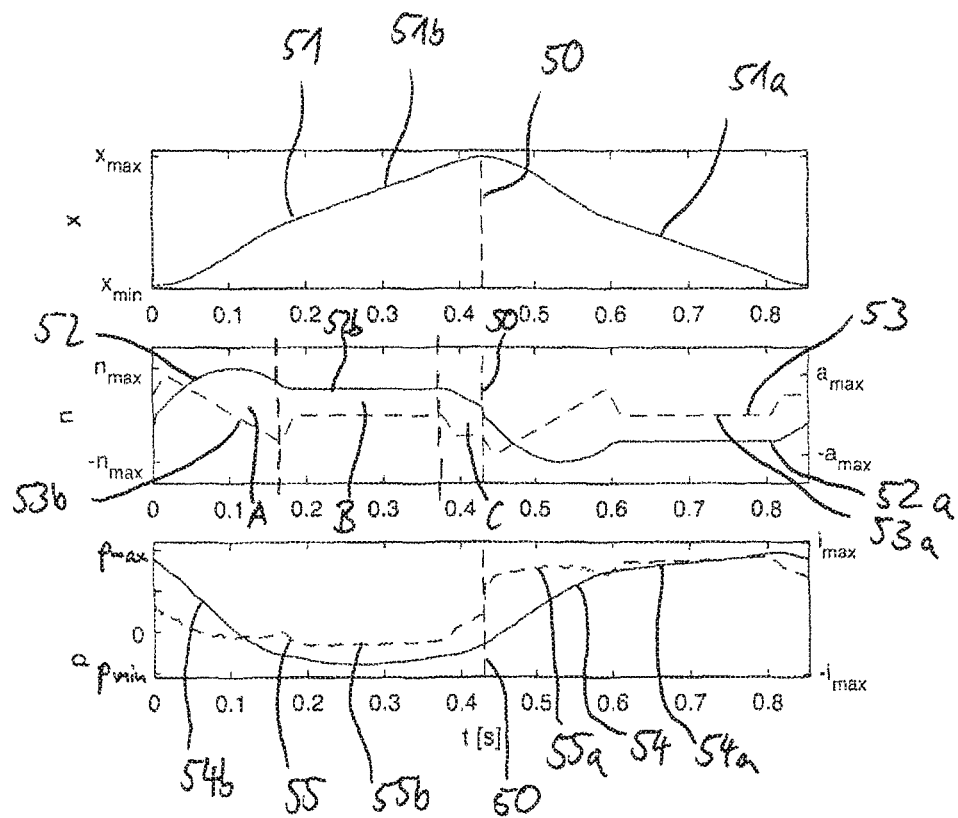
FIG. 4 provides curve diagrams for a pump cycle for a number of state variables that illustrate a specific movement example for the working piston.

FIG. 1 is a schematic depiction of a cardiac support system according to the invention, FIG. 2 is an acceleration-time diagram having a schematically depicted acceleration curve for the working piston of a drive device according to the invention during a half pump cycle, FIG. 3 is a flowchart for determining the position specification, the position regulation, and the regulation for the mean relative pressure according to the invention, and, FIG. 4 provides curve diagrams for a pump cycle for a number of state variables that illustrate a specific movement example for the working piston.

FIG. 1 is a schematic depiction of a cardiac support system according to the invention for a human heart 30. The cardiac support system according to the invention has an extracorporeal membrane blood pump 2 and an drive device 1. The drive device 1 and the membrane blood pump 2 are connected to one another via a pressure line 4. The membrane blood pump 2 has an inlet 2a and an outlet 2b. At the inlet 2a the membrane blood pump 2 is connected via an inlet cannula 21 to a left ventricle 31 of the heart 30. At the outlet 2b the membrane blood pump 2 is connected via an outlet cannula to a blood vessel (aorta) 32. In addition, the membrane blood pump 2 comprises a blood chamber 2d and an air chamber 2e that are separated from one another by a membrane 2c. The blood chamber 2d is in material exchange connection and pressure exchange connection with the inlet and outlet cannulas 21 and 22 and with the left ventricle 31 and the aorta 32—that is, the blood may flow out of the left ventricle 31 into the blood chamber 2d and from there into the aorta 32. The air chamber 2e is in material exchange connection and pressure exchanged connection with the pressure line 4 and the drive device 1—that is, air from the drive device 1 and the pressure line 4 also flows into the air chamber 2e. Via the membrane 2c of the membrane blood pump 2 a relative pressure may be transferred from the air chamber 2e to the blood chamber 2d, and thus from the drive device 1 to the blood chamber 2d. Relative pressure here shall be construed to mean an air pressure in the pressure line 4 relative to an ambient pressure.

The drive device 1 has a pneumatic cylinder 5 with a hollow cylindrical housing 5 and a working piston 6 that may be moved back and forth therein between two reversal points 9 and 10 in an oscillating manner. The reversal points 9 and 10 are not fixed points, but instead may be set in a targeted manner. The pneumatic cylinder is connected at its end faces to the pressure line 4. Towards the pressure line 4, the working piston 6 encloses a working chamber 7 with the housing 5. The working chamber 7 is in material exchange connection and pressure exchange connection with the pressure line 4. In the region of the working chamber 7, the pneumatic cylinder 3 furthermore has a equalizing valve 13 for compensating an air mass and/or a relative pressure in the working chamber 7 with the surroundings. The working piston 6 may be moved via a spindle 11 of an electric spindle motor 12. Moreover, the drive device 1 has a control unit 8 for controlling the movement of the working piston 6 and for controlling the equalizing valve 13 and has a user interface 14 for setting user-specific parameters.

For operating the drive device, the control unit 8 specifies the current for the spindle motor 12. How the current is specifically determined is explained further below in connection with FIG. 3. The spindle motor 12 drives the spindle 11. A rotational movement of the motor 12 is transmitted via the spindle 11 to a translatory movement of the working piston 6 so that the working piston 6 is moved back and forth between the reversal points 10 and 9 within the housing 5. If the working piston moves to the reversal point 9 located at the pressure line 4, the air in the working chamber 7 and in the pressure line is compressed. The relative pressure in the working chamber 7, pressure line 4, and air chamber 2e is also transmitted to the membrane 2c. Starting at a certain relative pressure, the membrane 2c begins to bulge in the direction of the cannulas 21 and 22 and to in turn build up a pressure on the blood disposed in the blood chamber 2d. Valves 2a' and 2b' are arranged at the inlet 2a and at the outlet 2b. The valve 2a' at the inlet 2a is closed during the evacuation phase and the valve 2b' at the outlet 2b is open so that the blood disposed in the blood chamber 2d may be pressed by the bulging of the membrane 2c through the outlet 2b into the outlet cannula 22 and from there into the blood vessel 32. It is optimal when the membrane 2c, upon reaching the reversal point 9, has completely expanded towards the cannulas 21, 22 but is not yet overexpanded. In this case the blood chamber is completely evacuated without damaging the membrane 2c.

Once the reversal point 9 has been reached, the working piston 6 moves in the opposite direction towards the reversal point 10. The relative pressure in the working chamber 7 drops rapidly because of this. Starting at a certain negative pressure, the membrane 2c of the membrane blood pump 2 begins to bulge towards the pressure line and away from the cannulas 21 and 22. This exerts a suction pressure on the blood chamber 2d. In the filling phase, the valve 2a' at the inlet 2a is open and the valve 2b' at the outlet 2b is closed. Due to the suction pressure, blood is now drawn out of the ventricle of the heart 31 through the inlet cannula 21 into the blood chamber 2d. It is optimal when the membrane, upon reaching the reversal point 10, has completely expanded in the direction of the pressure line 4 but is not overextended. In this case the blood chamber 2d is completely filled without damaging the membrane 2c.

The displacement volume of the membrane blood pump 2 may be set using the user interface 14. Moreover, the filling degree and evacuation degree for the membrane blood pump 2 may be adjusted independently of one another if, during operation, the behavior of the membrane 2c changes or the membrane 2c no longer exhibits optimal behavior or if there are deviations from optimal behavior in the filling phase or in the evacuation phase. The membrane blood pump is set using the user interface 14 using a visual examination of the membrane movement. High relative pressures in particular may be avoided in that the intensity of the setting is kept as low as possible.

The movement of the working piston is controlled by the control unit such that increased pump output compared to the prior art results. During operation of the drive device, therefore, the position of the working piston 6, the relative pressure in the working chamber 7, and the force of the working piston 6 are monitored continuously and deviations from a specification are corrected using targeted control.

One exemplary embodiment provides that the movement of the working piston 6 is controlled according to a position specification and the mean pressure in the working chamber 7 is simultaneously kept constant. An optimum position specification results when a temporal acceleration curve is maintained in a half pump cycle according to FIG. 2. How the specific position specification and the resultant current for the spindle motor 12 is determined shall be explained using FIG. 3. The acceleration curve depicted in the figure permits high pump output and smooth operation due to uniform pumping of the membrane blood pump 2 and smooth movement of the working piston 6 as well as a reduction in the risk of blood damage. The acceleration curve essentially has three phases A, B, C having durations $t_A$, $t_B$ and $t_C$, the working piston 6 being moved at a linearly decreasing acceleration in the first phase A, being moved unaccelerated in the second phase B, i.e., being moved at constant speed, and being slowed at a constant, negative acceleration in the third phase C. Between each two of the three phases there is a transition phase having duration ti, which transition phase continuously connects the three phases A, B, C of the acceleration curve to one another in order to permit smooth and/or low-load movement of the working piston between phases A, B and C.

During operation, the instantaneous position and speed of the working piston 6 is now measured every 1-10 ms, in particular every 2 ms, by means of a position sensor and there is a check that the position specification is being maintained. To this end the working pump 3 has a counter for Hall motor sensor increments (not shown) and at least one additional Hall sensor and/or one mechanical stop (neither shown here) on the working piston 6 that corresponds to a fixed reference position. The counter may be set back at start-up using the second Hall sensor or the mechanical stop. A speed of the working piston 6 is determined by the control unit 8 directly from the time measurement between two increments. The control unit 8 determines a deviation from the position specification and adjusts the current supplied to the spindle motor 12 based on this deviation such that the deviation is reduced. In addition, the relative pressure is measured every 2 ms and an instantaneous mean relative pressure is determined using the previous pump cycle. The control unit 8 determines a deviation from the specified mean relative pressure and controls the equalizing valve 13 such that the deviation from the specified mean relative pressure is reduced. This occurs in that the equalizing valve 13 is opened for a certain time both in the evacuation phase and in the filling phase. The opening duration for the equalizing valve 13 is determined in that three regions are distinguished for the mean pressure deviations and are associated with these desired mean pressure changes. The greater the mean deviation in the specific region, the greater the change in the mean pressure. The required opening duration is calculated as a function of the measured relative pressure (and of the estimated volume).

If the mean relative pressure is too high, the equalizing valve 13 is opened in the next evacuation phase in order to remove air. If the mean relative pressure is too low, the equalizing valve 13 is opened in the next filling phase in order to supply air.

Another exemplary embodiment provides for controlling the movement of the working piston 6 according to a relative pressure specification and minimizing and keeping constant the dead volume of the cylinder using the equalizing valve 13. In the second phase, the working piston is moved such that the relative pressure is kept constant. During operation, the instantaneous relative pressure in the working chamber 7 is measured every 1-10 ms, in particular every 2 ms. The control unit 8 determines a deviation of the instantaneous relative pressure from the specification and adjusts the current strength for the spindle motor 12 such that the deviation from the relative pressure specification is reduced during the further movement of the working piston 6. In addition, the position of the working piston 6 is continuously monitored by means of a position sensor, the control unit 8 checking whether the working piston 6 attains a desired end position. If this is not the case, depending on whether the desired end position was exceeded or not attained, the equalizing valve 13 is opened once for a certain period in the filling phase or in the evacuation phase in order to supply air to the working chamber 7 or to remove air. The equalizing valve 13 is opened for a longer or shorter period depending on the magnitude of the deviation from the predefined end position.

Another exemplary embodiment provides that the relative pressure regulation described above is subordinate to a speed regulation or position regulation, since in this example regulation solely of pressure is susceptible to faults in terms of changes in load or leakage. In this case, the current is adjusted based on a pressure deviation from the relative pressure specification in the context of the speed specification or position specification. That is, the pressure change specification first goes into the speed specification or position specification. Thus, based on the pressure change specification, the control unit first determines a speed change specification or position change specification, on the basis of which the current adjustment is calculated. A maximum limit for the speed, which limit must not be exceeded during operation, is maintained in a simple manner, in particular due to the subordinate speed regulation.

Another exemplary embodiment provides that the control unit controls the movement of the working piston 6 according to a force specification for the working piston 6, the sum of inertia force of the working piston 6 and load of the working piston 6 being kept constant in the second phase. The force specification for the working piston 6 is converted to a torque specification for the spindle motor 12 using the kinematic relationships between the working piston 6 and the spindle motor 12. During operation, the torque of the spindle motor 12, which torque overcomes the inertia force of the working piston 6 and the load of the working piston, is monitored continuously. To this end, the instantaneous position and the instantaneous speed are measured every 1-10 ms, in particular every 2 ms, using the position sensor, and the instantaneous relative pressure is measured using the pressure sensor. The control unit 8 determines the momentary torque from these values and determines a deviation of the momentary torque from the specification. The control unit 8 adjusts the current such that the deviation is reduced. At the same time, as with the pressure regulation, the control unit, using the equalizing valve 13, keeps the air mass in the end position as small as possible in the evacuation phase in that the equalizing valve 13 is opened for an appropriate period once per pump cycle if there is a pressure deviation. When there force regulation, as well, it is necessary to specify the end positions of the working piston 6 separately, because otherwise the working piston 6 would run against the housing wall. A position sensor monitors attainment of each end position. During operation, the position sensor measures whether the specific end position is attained. If both end positions are not attained, the force may be appropriately adjusted by adjusting the current strength. If the distance from the working piston 6 to the housing wall becomes to slight, on the other hand the movement direction of the working piston 6 must be modified immediately.

The quantity of the blood conveyed by the membrane blood pump (displacement volume) may be adjusted using the user interface 14. Furthermore, the degree of filling and degree of evacuation may be adjusted separately from one another. This shall be explained in the following using the example of position regulation. If, for example, the degree of filling is to be increased or decreased, the piston stroke in the filling phase is increased or decreased, if there is still a stroke reserve, and a change is made from regulating the mean relative pressure to regulating the mean evacuation pressure using the equalizing valve 13. Provided no other changes to the piston stroke have been made, after a predefined number of pump cycles, according to the last change to the filling degree and/or evacuation degree, a change is made to regulation of the mean relative pressure. The predefined number of pump cycles is preferably between 20 and 100, in particular 50. However, if there is no more piston stroke available, the mean relative pressure is reduced or increased. Analogously, the degree of evacuation is changed. If the degree of evacuation is to be increased or reduced, the piston stroke in the evacuation phase is increased or reduced, provided there is still stroke reserve available, and there is a change from regulating mean relative pressure to regulating the mean filling pressure using the equalizing valve 13. Provided no other changes to the piston stroke have been made, after a predefined number of pump cycles a change is made back to regulating the mean relative pressure. The predefined number of pump cycles is preferably between 20 and 100, in particular 50. However, if there is no more piston stroke available, the mean relative pressure is reduced or increased.

During the relative pressure regulation, the pump rate is set based on the required fluid flow. The filling and evacuation behavior is set using the filling pressure and evacuation pressure. The user may extend the evacuation duration in order to reduce the filling pressures.

FIG. 3 depicts a flow chart for determining the position specification, position regulation, and regulation for the mean relative pressure according to the invention. In a reference generator 40, first a reference trajectory is determined and a mean relative pressure is specified. The starting point for the reference trajectory is a qualitative temporal curve of the speed and the acceleration, which is characterized by the specification of the first through third phases. FIG. 2 illustrates the qualitative temporal curve of the acceleration, for example. The qualitative acceleration curve is then adjusted to a specific membrane fluid pump-cannulas combination P by the specific selection of the trajectory parameters compression duration $t_C$, pump duration $t_P$, increase in compression m and piston stroke dx. This reference trajectory is then scaled using the selection of specific user settings. The user settings may be a pump rate r, a relative evacuation duration s (duration of the evacuation phase for a half pump cycle), and change specifications for a degree of filling and degree of evacuation. The pump rate r is set according to the blood flow required. The relative evacuation duration in the present example is preferably set to approximately 50%. Setting for filling and evacuation in particular limits the filling pressure and evacuation pressure. The user settings are converted to the trajectory parameters in the control unit, and the trajectory parameters are adjusted appropriately, so that an adjusted reference trajectory results. The reference trajectory supplies a specification for the target acceleration $a_S$, the target speed $v_S$, and the target position $x_S$.

The specifications for the reference trajectory are transmitted to the position regulation 41. The target acceleration and target speed are used in the preliminary control for determining the torque $M_{FF}$ for the spindle motor 12 for overcoming the load L, the inertia J, and the friction $\mu_0$, $\mu^*v_s$ of the working piston. The friction $\mu_0$, $\mu^*v_s$ is estimated using a model for a total frictional torque b ($\mu_0+\mu^*v_s$). In the model, the total frictional torque is equal to the sum of static friction $\mu_0$ and slide friction $\mu^*v_s$, the sum then being scaled with a factor b. The total frictional torque for the position specification may be adjusted using the individual factor b. The frictional torque represents a temporally modifiable model parameter. The change in the frictional torque results, for example, from aging of the pneumatic cylinder and short-term influences such as, e.g. fluctuations in temperature.

The target speed and the target position are also transmitted to the feedback. The actual position x and actual speed v are measured in the drive system (pneumatic cylinder) 42. They are then also transmitted to the feedback. The differences $x_s-x$ between the target position and the actual position and $v_s-v$ between the target speed and the actual speed are determined in the feedback. A torque correction $M_{FB}$ is determined based on the position and speed differences.

The torques $M_{FF}$ and $M_{FB}$ are then added and converted via an electronics model having an inverse current regulator to a current i. The current i is supplied to the drive system.

The target pressure specification $p_T$ from the reference generator may be a specification for the mean relative pressure, for instance, which must be kept constant. The target pressure specification is transmitted to the air mass regulator 43. An actual pressure is measured in the drive system (pneumatic cylinder). The actual pressure is transmitted to the air mass regulator 43 and a pressure difference is calculated. Based on the pressure difference, a target pressure change specification dp is transmitted to a valve model for the equalizing valve 13. The valve model converts the target pressure change specification to a valve opening time o and outputs this to the equalizing valve 13 in the drive system.

The position-regulated drive in the drive system 42 sets the position x of the working piston at any point in time. The instantaneously measured relative pressure p is the reaction of the connected system to the position x. The relative pressure is influenced by the air mass, volume and loads.

The valve model and the friction model may be adjusted automatically using a model adjustment 44 during the course of the regulation. By comparing the target pressure change specification dp to the subsequently measured pressure p, a valve constant $k_V$ may be adjusted such that during the course of the regulation the target pressure change specification is better maintained. The friction adjustment occurs when the difference between target and actual position exceeds a specific value and is retained for a specific period, as well as when the current i moves in a certain range. The total drive torque is adjusted using a change in the scaling factor b.

FIG. 4 provides curve diagrams of state variables for a pump cycle, the state variables describing a qualitative temporal curve of the state of the working piston 6. Each of the curve diagrams illustrates one filling and one evacuation phase that are visually separated from one another by a broken line 50. The curve 51 illustrates a temporal position curve. The segment 51a illustrates the evacuation phase, while the segment 51b illustrates the filling phase. According to the curve 50, the working piston 6 moves from the end position of a previous evacuation phase at $x=x_{min}$ to the end position of the filling phase 51b at $x=x_{max}$ and from there back to the end position of the evacuation phase 51a at $x=x_{min}$ mm.

The curve 52 illustrates a speed curve, the segment 52a illustrating the evacuation phase and the segment 52b illustrating the filling phase. The speed of the spindle motor 12 may be converted to a speed of the working piston 6 using the kinematic relationships between the spindle motor 12 and the working piston 6. The speed of the working piston 6 increases in the first part of the filling phase 52b, which corresponds to the first phase A, initially from a stop of the working piston 6 to a speed that is greater than a speed of the working piston 6 at the end of the first phase A. The speed remains substantially constant in the middle part of the filling phase 52b, which corresponds to the second phases B. The speed decreases substantially linearly in the last part of the filling phase 52b, which corresponds to the third phase C. The evacuation phase 52a illustrates a similar curve with the opposite mathematical operator for the speed.

The curve 53 illustrates an acceleration curve, the segment 53a illustrating the evacuation phase and the segment 53b the filling phase.

The qualitative curve from FIG. 2 may be seen in the filling phase 53b. The filling phase 53b begins with a first phase A substantially linearly decreasing acceleration, then exhibits a second phase B without acceleration (a=0), and ends with a third phase C having constant negative acceleration. The evacuation phase 52a illustrates a similar curve with the opposite mathematical operator for the acceleration.

The illustrated speed curve and acceleration curve allow for a high pump output and a smooth operation using uniform pumping of the membrane blood pump 2 and smooth movement of the working piston 6, as well as a decrease in the risk of blood damage.

The curve 54 illustrates a relative pressure curve, segment 54a illustrating the evacuation phase and segment 54b the filling phase. The relative pressure increases relatively rapidly at the beginning of the evacuation phase 54a and then remains at a constant high level from about a third of the evacuation phase 54a until the end of the evacuation phase 54a. The reverse behavior may be seen in the filling phase 54b. Given the relative pressure curve, it is clear that the relative pressure is substantially constant due to the special position specification according to curves 51, 52, and 53 in a vast majority of each half pump cycle. A constant pressure offers the advantage that sufficient regulation reserve is available for compensating faults.

The curve 55 illustrates a current curve, the segment 55a illustrating the evacuation phase and the segment 55b the filling phase. The current also remains relatively constant over a vast majority of a half pumping cycle due to the special position specification according to curves 51, 52 and 53. A constant current also permits sufficient regulation reserve for compensating faults.

The control unit, which may also be referred to as a controller, may include a processor. The processor may include one or more devices operable to execute logic. Examples of the processor include a general processor, a central processing unit, a microcontroller, an application specific integrated circuit (ASIC), a field programmable gate array (FPGA), a digital signal processor, a digital circuit, and/or an analog circuit. The control unit or the controller may include a memory and/or be in communication with the memory. In some examples, the logic executable by the processor may include computer executable instructions or computer code embodied in the memory. The logic, when executed by the processor, causes the processor to perform one or more of the features described herein as performed by the control unit. The processing capability of the controller may be distributed among multiple entities, such as among multiple processors and memories. In some examples, the processor may be in communication with one or more additional devices, such as the user interface.

The memory may include any device for storing, retrieving data, or any combination thereof. The memory may include non-volatile and/or volatile memory, such as a random access memory (RAM), a read-only memory (ROM), an erasable programmable read-only memory (EPROM), or a flash memory. Alternatively or in addition, the memory may include an optical, magnetic (hard-drive), or any other form of data storage device.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. A drive device for a membrane fluid pump, the drive device comprising:
a working pump, the working pump connected to the membrane fluid pump via a pressure line in order to drive the membrane fluid pump, and the working pump having a hollow cylinder and a working piston configured to oscillate axially therein between two reversal points for contraction and expansion of a working chamber in the working pump, the working chamber being in a pressure exchanging connection with the pressure line; and
a control unit configured to control a movement of the working piston between the two reversal points, the controlled movement of the working piston comprising three temporally successive phases,
wherein in a first phase the working piston is accelerated to a speed that is greater than a speed at the end of the first phase,
wherein in a second phase the working piston is moved such that a specified speed of the working piston, a specified relative pressure in the working chamber, or a specified force of the working piston is kept substantially constant,
and
wherein in a third phase the working piston is moved at a negative acceleration.

2. The drive device of claim 1, wherein the control unit is configured to control the movement of the working piston according to a temporal position specification for the working piston, the speed of the working piston kept substantially constant in the second phase, and/or the control unit is configured to control the movement of the working piston according to a temporal relative pressure specification for the working chamber, the relative pressure in the working chamber kept substantially constant in the second phase, and/or the control unit is configured to control the movement of the working piston according to a temporal force specification for the working piston, the force of the working piston kept substantially constant in the second phase.

3. The drive device of claim 2, wherein the force of the working piston includes a load and an inertia of the working piston.

4. The drive device of claim 2, wherein the control unit is configured to determine the temporal position specification based on the temporal relative pressure specification, and to control the movement of the working piston according to the position specification.

5. The drive device of claim 2, wherein the temporal position specification includes a temporal speed specification and/or a temporal acceleration specification.

6. The drive device of claim 1, wherein the working pump comprises an equalizing valve for changing an air mass and/or a relative pressure in the working chamber, and the control unit is configured to control the equalizing valve according to a specification for the air mass and/or a specification for the relative pressure.

7. The drive device of claim 2, wherein the control unit is configured to determine the temporal position specification based on a reference trajectory of the working piston, wherein the reference trajectory takes into consideration a specified duration of the first phase, a specified duration of the second phase, a specified change in the acceleration of the piston in the first phase, a specified piston stroke, a specified maximum relative pressure, a specified pump rate, a specified relative evacuation duration, a specified filling degree, a specified evacuation degree, specified characteristic values for a membrane fluid pump to be connected.

8. The drive device of claim 2, wherein the drive device has an electric spindle motor for driving the working piston, and the control unit, in order to control the movement of the working piston according to the temporal position specification, is configured to determine a drive current strength for the spindle motor based on an estimated required torque for the spindle motor, wherein a load of the working piston, inertia of the working piston, estimated friction of the working piston, and/or a torque correction for compensating a position deviation and/or a speed deviation of the working piston from the temporal position specification factor into the torque.

9. The drive device of claim 8, wherein a position sensor is configured to measure during operation an instantaneous position and/or an instantaneous speed of the working piston, and wherein the control unit is configured to determine a position deviation and/or a speed deviation from the temporal position specification, to determine the torque correction based on the position deviation and/or the speed deviation, and to adjust the drive current strength such that the position deviation and/or the speed deviation of the working piston is reduced.

10. The drive device of claim 1 comprising a user interface by which user-specific parameters are settable during operation, the user-specific parameters including a degree of filling, a degree of evacuation of the membrane fluid pump, a piston stroke, a mean relative pressure, a relative evacuation duration, an evacuation pressure, a filling pressure, and/or a pump rate.

11. The drive device of claim 10, wherein the control unit is configured to adjust a temporal position specification, a temporal relative pressure specification, and/or the temporal force specification, for controlling the movement of the working piston, and/or to adjust a specification for an air mass, the specification for the relative pressure, and/or the specification for one of the two or both reversal points for controlling an equalizing valve during operation in response to a change in the user-specific parameters.

12. The drive device of claim 6, wherein the control unit is configured to set a filling degree for the membrane fluid pump by a change of a piston stroke and control of the equalizing valve according to a specification for a mean evacuation pressure in the working chamber or by a change of a mean relative pressure using the equalizing valve, and/or wherein the control unit is configured to set an evacuation degree by a change of the piston stroke and control of the equalizing valve according to a specification for a mean filling pressure in the working chamber, and/or by a change of the mean relative pressure using the equalizing valve.

13. The drive device of claim 1, wherein an inlet cannula connected to the membrane fluid pump is configured to supply a fluid to the membrane fluid pump, and an outlet cannula connected to the membrane fluid pump is configured to conduct a fluid out of the membrane fluid pump.

14. A cardiac support system comprising:
a membrane blood pump;
an inlet cannula connected to the membrane blood pump, the inlet cannula configured to supply blood from a ventricle and/or an atrium of a heart to the membrane blood pump;

an outlet cannula connected to the membrane blood pump, the outlet cannula configured to conduct the blood out of the membrane blood pump into a blood vessel;

a working pump, the working pump connected to the membrane blood pump via a pressure line in order to drive the membrane blood pump, and the working pump having a hollow cylinder and a working piston configured to oscillate axially therein between two reversal points for contraction and expansion of a working chamber in the working pump, the working chamber being in a pressure exchanging connection with the pressure line; and a control unit configured to control a movement of the working piston between the two reversal points, the controlled movement of the working piston comprising three temporally successive phases, wherein in a first phase the working piston is accelerated to a speed that is greater than a speed at the end of the first phase, wherein in a second phase the working piston is moved such that a specified speed of the working piston, a specified relative pressure in the working chamber, or a specified force of the working piston is kept substantially constant, and wherein in a third phase the working piston is moved at a negative acceleration.

15. A method for operating a drive device for a membrane fluid pump, the drive device comprising a working pump, the working pump connected to the membrane fluid pump via a pressure line in order to drive the membrane fluid pump, and the working pump having a hollow cylinder and a working piston configured to oscillate axially therein between two reversal points for contraction and expansion of a working chamber in the working pump, the working chamber being in a pressure exchanging connection with the pressure line, the method comprising moving the working piston in three temporally successive phases by:

accelerating, in a first phase, the working piston to a speed that is greater than a speed of the working piston at an end of the first phase, moving, in a second phase, the working piston such that a predefined speed of the working piston, a predefined relative pressure in the working chamber, or a predefined force of the working piston is kept substantially constant, and deaccelerating the working piston in a third phase.

16. The method of claim 15, wherein the moving the working piston in three temporally successive phases comprises controlling the movement of the working piston according to a temporal position specification for the working piston, keeping the speed of the working piston substantially constant in the second phase, and/or wherein the moving the working piston in three temporally successive phases comprises controlling the movement of the working piston according to a temporal relative pressure specification for the working chamber, keeping the relative pressure in the working chamber substantially constant in the second phase, and/or wherein the moving the working piston in three temporally successive phases comprises controlling the movement of the working piston according to a temporal force specification for the working piston, and keeping the force of the working piston substantially constant.

17. The method of claim 16 further comprising determining the temporal position specification based on the temporal relative pressure specification, and controlling the movement of the working piston according to the temporal position specification.

18. The method of claim 16, wherein the moving the working piston in three temporally successive phases comprises controlling movement of the working piston according to the temporal position specification in the first phase and in the third phase, and controlling according to the temporal relative pressure specification and/or the temporal force specification in the second phase.

19. The method of claim 16, wherein the working pump comprises an equalizing valve for changing an air mass and/or a relative pressure in the working chamber, and wherein the moving the working piston in three temporally successive phases comprises controlling the movement of the working piston according to the temporal position specification and controlling the equalizing valve according to a specification for a mean relative pressure, or controlling the movement of the working piston according to the temporal relative pressure specification or according to the temporal force specification and controlling the equalizing valve such that the air mass at the end of an evacuation phase is minimal.

20. The method of claim 16 further comprising determining the temporal position specification based on a reference trajectory for the working piston, the reference trajectory taking into consideration a specified duration of the first phase, a specified duration of the second phase, a specified change in the acceleration of the working piston in the first phase, a specified piston stroke, a specified maximum relative pressure, a specified pump rate, a specified relative evacuation duration, a specified filling degree, a specified evacuation degree, specified characteristic values for a membrane fluid pump to be connected, in particular a displacement volume of the membrane fluid pump, specified characteristic values for an inlet cannula that may be connected to the membrane fluid pump, and/or specified characteristic values for an outlet cannula that may be connected to the membrane fluid pump.

21. The method of claim 15, wherein for driving the working piston the drive device has an electric spindle motor, and, for controlling the movement of the working piston according to a temporal position specification, determining a drive current strength for the spindle motor based on an estimated required torque for the spindle motor, wherein a load of the working piston, inertia of the working piston, estimated friction of the working piston, and/or a torque correction for compensating a position deviation and/or a speed deviation of the working piston from the temporal position specification factor into the torque.

22. The method of claim 21 further comprising measuring, during operation, an instantaneous position and/or an instantaneous speed of the working piston by a position sensor; determining a position deviation and/or a speed deviation from the temporal position; determining the torque correction based on the position deviation and/or the speed deviation; and adjusting the drive current strength such that the position deviation and/or the speed deviation of the working piston from the temporal position specification is reduced.

23. The method of claim 15 further comprising setting user-specific parameters during operation, the user-specific parameters including a degree of filling and/or a degree of evacuation of the membrane fluid pump, a piston stroke, a mean relative pressure, a relative evacuation duration, an evacuation pressure, a filling pressure, and/or a pump rate; and adjusting, in response to a change in the user-specific parameters, a temporal position specification, a temporal relative pressure specification, and/or the temporal force specification for controlling the movement of the working piston, and/or a specification for an air mass, the specification for the relative pressure, and/or the specification for the air mass at one of the two or at both reversal points for controlling an equalizing valve for changing the air mass and/or the relative pressure in the working chamber.

24. The method of claim 19 further comprising setting a specified filling degree of the membrane fluid pump by changing a piston stroke and controlling the equalizing valve according to a specification for a mean evacuation pressure in the working chamber or by changing the mean relative pressure using the equalizing valve, and/or a specified evacuation degree is set by changing a piston stroke and controlling the equalizing valve according to a specification for a mean filling pressure in the working chamber and/or by changing the mean relative pressure via the equalizing valve.

* * * * *